United States Patent [19]
De Brabander et al.

[11] Patent Number: 5,955,485
[45] Date of Patent: Sep. 21, 1999

[54] USE OF FUSED BENZOTHIAZOLES AS NEUROPROTECTANTS

[75] Inventors: Marc Joris De Brabander, Zoersel; Anne Simone Josephine Lesage, Halle-Zoersel; Josepha Eduarda Maria Francisca Leysen, Oud-Turnhout, all of Belgium

[73] Assignee: Janssen Pharmaceutica, N.V., Beerse, Belgium

[21] Appl. No.: 08/894,121

[22] PCT Filed: Feb. 14, 1996

[86] PCT No.: PCT/EP96/00677

§ 371 Date: Aug. 12, 1997

§ 102(e) Date: Aug. 12, 1997

[87] PCT Pub. No.: WO96/25931

PCT Pub. Date: Aug. 29, 1996

[30] Foreign Application Priority Data

Feb. 23, 1995 [EP] European Pat. Off. .............. 95200446

[51] Int. Cl.⁶ ....................... A61K 31/425; C07D 513/02
[52] U.S. Cl. ............................................ 514/366; 548/151
[58] Field of Search .............................. 514/366; 548/151

[56] References Cited

U.S. PATENT DOCUMENTS

| | | | |
|---|---|---|---|
| 4,262,004 | 4/1981 | Sipido | 424/270 |
| 4,340,738 | 7/1982 | Sipido | 548/151 |
| 4,364,942 | 12/1982 | Sipido | 424/245 |

OTHER PUBLICATIONS

J. Neural Transm., Suppl., vol. 43, 1994, pp. 183–201, XP000604350 KW. Lange et al. "Neuroprotection by Dopamine Agonists." see pp. 183–189.

Progress Neurobiol., vol. 48, No. 1, 1996, pp. 1–19, XP000604403 M. Ebadi et al.; Oxidative Stress and Antioxidant Therapy in Parkinson's Disease.

Neurobiol. Aging, vol. 16, No. 4, 1995, pp. 661–674, SP000604397 G. Benzi et al: "Are Reactive Oxygen Species Involved in Alzheimer's Disease?".

*Primary Examiner*—Robert W. Ramsuer
*Assistant Examiner*—Joseph Murray
*Attorney, Agent, or Firm*—Ellen Ciambrone Coletti

[57] ABSTRACT

The present invention is concerned with the method of using a 2,3-dihydro-imidazo[2,1-b]benzothiazole derivative for the manufacture of a medicament for the therapeutic or prophylactic treatment of humans suffering from ageing of, or degenerative diseases of the nervous and vascular system which are associated with oxidative stress.

9 Claims, No Drawings

USE OF FUSED BENZOTHIAZOLES AS NEUROPROTECTANTS

CROSS-REFERENCE TO RELATED APPLICATION APPLICATIONS

This application is based upon PCT Application Serial No. PCT/EP 96/00677, filed Feb. 14, 1996, which claims priority from European Patent Application Serial No. 95.200.446.3, filed on Feb. 23, 1995.

The present invention is concerned with the use of a 2,3-dihydro-imidazo[2,1-b]benzothiazole derivative for the manufacture of a medicament for the therapeutic or prophylactic treatment of humans suffering from ageing of, or degenerative diseases of the nervous and vascular system which are associated with oxidative stress.

2,3-Dihydro-imidazo[2,1-b]benzothiazole derivatives are disclosed in U.S. Pat. No. 4,262,004 as agents inhibiting the enzyme monoamine oxidase (MAO) and having therapeutic potential for treating depression and Parkinsonism. Experiments now show that certain 2,3-dihydro-imidazo[2,1-b]benzothiazole derivatives disclosed therein have potent antioxidant activity both in vitro and in vivo. In view of their antioxidant properties, these derivatives have therapeutical utility in the treatment of degenerative diseases, as well as ageing, of the nervous and vascular system which are associated with oxidative stress.

Consequently, the present invention is concerned with the use of 2,3-dihydro-imidazo[2,1-b]benzothiazole derivatives, the pharmaceutically acceptable acid addition salts, the stereochemically isomeric forms, and any mixtures of said derivatives, salts and stereoisomers, for the manufacture of a medicament for the therapeutic or prophylactic treatment of humans suffering from ageing of, or degenerative diseases of the nervous and vascular system which are associated with oxidative stress, said derivatives having the formula (I):

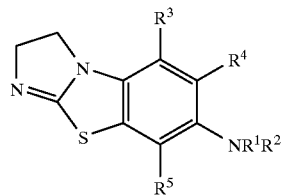

wherein $R^1$ represents $C_{1-10}$alkyl or $C_{5-12}$cycloalkyl, $R^2$ represents hydrogen or $C_{1-10}$alkyl; and $R^3$, $R^4$ and $R^5$ each independently represent hydrogen or $C_{1-4}$alkyl.

The invention also concerns a method of treating patients suffering from ageing and degenerative diseases of the nervous and vascular system which are associated with oxidative stress, by administering to said patients an amount of a 2,3-dihydro-imidazo[2,1-b]benzothiazole derivative of formula (I) effective in improving, halting, retarding or palliating the course and/or effects of said ageing and degenerative diseases.

$C_{1-4}$alkyl defines methyl, ethyl, propyl, butyl and the branched isomers thereof. $C_{1-10}$alkyl defines straight and branched saturated hydrocarbon radicals having from 1 to 10 carbon atoms, e.g. methyl, ethyl, propyl, butyl, pentyl, hexyl, heptyl, octyl, nonyl, decyl and the branched isomers thereof. $C_{5-12}$cycloalkyl defines monocylic and where possible also bi- and tricyclic saturated hydrocarbon radicals having from 5 to 12 carbon atoms, e.g. cyclopentyl, cyclohexyl, cycloheptyl cyclooctyl, cyclononyl, cyclodecyl, cycloundecyl, cyclododecyl, bicyclo[2.1.1]hexyl, bicyclo[2.2.1]heptyl (norbornyl), bicyclo[2.2.2]octyl, tricyclo[3.3.1.1$^{3,7}$]decyl (adamantyl) and the like cycloalkyl radicals.

Preferred are the compounds wherein $R^1$ represents $C_{4-10}$alkyl or $C_{7-10}$cycloalkyl; and $R^2$ represents hydrogen. $R^3$, $R^4$ and $R^5$ preferably represent hydrogen; and $R^3$ and $R^5$ also may represent methyl, ethyl, 2-propyl and 2-methyl-2-propyl. Especially preferred are the compounds wherein $R^1$ represents a straight $C_{6-10}$alkyl group, a $C_{4-10}$alkyl group branched in α- or β-position or a monocyclic $C_{7-10}$cycloalkyl group.

Specific compounds according to the invention include:
N-cycloheptyl-2,3dihydro-imidazo[2,1-b]benzothiazol-7-amine; and
N-hexyl-2,3-dihydro-imidazo[2,1-b]benzothiazol-7-amine.

The compounds of formula (I) may be prepared following the procedures described in U.S. Pat. No. 4,262,004. As they have basic properties, these compounds may be converted into their pharmaceutically acceptable acid addition salt forms by treatment with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids. The term addition salt as used hereinabove also comprises the solvates which the compounds of formula (I) as well as the salts thereof, are able to form. Such solvates are for example hydrates, alcoholates and the like. The preferred acid addition salt of N-cycloheptyl-2,3dihydro-imidazo[2,1-b]benzothiazol-7-amine is the dihydrochloride salt. Salts which are not pharmaceutically acceptable may be useful in the preparation of the compounds of formula (I) and of compositions comprising such compounds.

Oxidative stress refers to phenomena related to the action, in particular the deleterious effects, of oxidants within tissue. Endogenous strong oxidants are for example superoxide $(O_2^-\cdot)$, hydrogen peroxide $(H_2O_2)$ and the hydroxyl radical $(HO\cdot)$. The tissue may be central, peripheral or medullar, and in particular belongs to the vascular system, the nervous system, the kidneys, the liver, the heart, the pancreas, the parathyroid glands and the gonads. Oxidative stress in tissue cells leads to DNA damage, protein damage and to lipid peroxidation, the latter giving rise to changes in cell membrane integrity and function. Oxidative injury by oxygen derived free radicals is nowadays generally considered to be a key step in the initiation and progression of neurodegenerative disorders.

Therapeutic treatment comprises the administration of such a derivative in an amount effective in improving, halting, retarding or palliating the course and/or effects of said degenerative diseases of the nervous and vascular system. Prophylactic treatment comprises the administration of such a derivative in an amount effective in preventing or delaying the onset and evolution of ageing of, or degenerative diseases of the nervous and vascular system.

The antioxidant activity of 2,3-dihydro-imidazo[2,1-b]benzothiazole derivatives can be demonstrated in vitro by their ability to scavenge free radicals and thus prevent radical-induced lipid peroxidation and cytotoxicity. In cultures of neuronal cells, they can effectively substitute the known endogenous antioxidant vitamin E (α-tocopherol).

The antioxidant activity of the compounds of formula (I) can also be seen in their protecting human fibroblasts in culture against cell death induced by glutathione depletion in the culture medium. The antioxidant activity of the compounds of formula (I) appears to be proportional to their lipophilicity, i.e. the antioxidant activity increases as $R^1$ represents a larger alkyl or cycloalkyl group.

Diseases and conditions of the nervous and vascular system which are associated with oxidative stress and which are considered to be susceptible to treatment with the compounds of formula (I) are normal and pathological degeneration of the nervous system. In particular, said compounds may have therapeutic value in preventing or treating neuronal loss from the central and peripheral nervous system which is associated with oxidative damage or injury, e.g. in thromboembolic stroke, cerebral stroke, haemorrhagic stroke, cerebral ischaemia, cerebral vasospasm, cerebral ageing, cerebral or spinal trauma, cardiac arrest, arterial hypotension, cardiac or pulmonary surgery, severe hypoglycaemia, anoxia, hypoxia, perinatal asphyxia; and in alleviating neurodegenerative disorders wherein oxidative metabolic processes play a role such as, Huntington's chorea, Alzheimer's disease, senile dementia, Pick's disease, Korsakoff's disease, olivoponto cerebellar atrophy, amyotrophic lateral sclerosis, Parkinson's disease, Down's syndrome, glutaric acidaemia, epilepsy, convulsive states, multi-infarct dementia, and viral-infection induced neurodegeneration, in particular neuro-AIDS encompassing dementia, cognitive difficulties, progressive dysarthria, ataxia, neuro- and myopathies associated with HIV infection, or any disease that involves cerebral inflammation.

The compounds of formula (I), and in particular the preferred compound N-cycloheptyl-2,3-dihydro-imidazo[2,1-b]benzothiazol-7-amine dihydrochloride, are expected to be especially useful in treating patients suffering from Alzheimer's Disease and patients suffering from AIDS and in particular neuro-AIDS. Alzheimer's disease is a kind of progressive dementia which is characterized by impaired memory, language, visuo-spatial skills and behaviour. Neuro-AIDS is a typical condition associated with HIV infection and manifests itself as an infection of the central and peripheral nervous system characterized by progressive demyelination.

Further, in view of their anti-oxidant properties, the compounds of formula (I) may also have utility in preventing or treating normal and pathological degeneration of the vascular system such as atherogenesis, atheromatosis (fatty degeneration of the endothelium of arteries), arteriosclerosis, atherosclerosis, vascular hypertrophy associated with hypertension, hyperlipoproteinaemia, and normal vascular degeneration through ageing; vasculopathy of the gonads and pancreas; parathyroidal reactive hyperplasia; chronic renal disease; in neoplastic diseases; and in inflammatory diseases.

Pharmaceutical compositions of the compounds of formula (I) suitable as medicaments according to the present invention comprise one or more excipients or carriers as known in the art. By appropriately selecting one or more of these excipients or carriers, the pharmaceutical compositions are adapted for oral, rectal, vaginal, topical, parenteral (including intramuscular, subcutaneous and intravenous) or implant administration or in a form suitable for administration by inhalation or insufflation. The formulations may, where appropriate, be conveniently presented in discrete dosage units.

Processes of preparing such compositions are well known in the art and are characterized in that the active ingredient and the excipient are intimately mixed with one another. All processes include the step of bringing into association the active compound with liquid carriers or finely divided solid carriers or both and then, if necessary, shaping the product into the desired formulation.

For oral administration, the pharmaceutical compositions may take the form of solid dose forms, for example, tablets or capsules prepared by conventional means with pharmaceutically acceptable excipients such as binding agents (e.g. pregelatinised starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art.

Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For topical administration in the mouth, the pharmaceutical compositions may take the form of buccal or sublingual tablets, drops or lozenges formulated in conventional manner.

For topical administration to the epidermis the compounds of the invention may be formulated as creams, gels, ointments or lotions or as transdermal patches. Such compositions may, for example, be formulated with an aqueous or oily base with the addition of suitable thickening, gelling, emulsifying, stabilising, dispersing, suspending, and/or colouring agents.

The compounds of formula (I) may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example as a sparingly soluble salt.

The compounds of formula (I) may be formulated for parenteral administration by injection, conveniently intravenous, intramuscular or subcutaneous injection, for example by bolus injection or continuous intravenous infusion. Formulations for injection may be presented in unit dosage form e.g. in ampoules, or in multidose containers with an added preservative. The compositions may take such forms as suspensions, solutions or emulsions in oily or aqueous vehicles, and may contain form ulatory agents such as suspending, stabilising and/or dispersing agents. Alternatively, the active ingredient may be in powder form for constitution with a suitable vehicle, e.g. sterile pyrogen-free water.

The compounds of formula (I) may also be formulated in rectal compositions such as suppositories or retention enemas, e.g. containing conventional suppository bases such as cocoa butter or other glycerides.

For intranasal administration the compounds of formula (I) may be used, for example, as a liquid spray, as a powder or in the form of drops.

For administration by inhalation the compounds of formula (I) are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, 1,1,1,2-tetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch. Any of the pharmaceutical compositions described above may be presented in a conventional manner associated with controlled release forms.

In order to increase the bio-availability of the compounds of formula (I), they may be formulated advantageously with appropriate cyclodextrins. Appropriate cyclodextrins are α-, β-, γ-cyclodextrins, or ethers, or mixed ethers thereof wherein one or more of the hydroxy groups of the anhydroglucose units of the cyclodextrin are substituted with $C_{1-6}$alkyl, particularly methyl, ethyl or isopropyl; hydroxy$C_{1-6}$alkyl, particularly hydroxyethyl, hydroxypropyl or hydroxybutyl; carboxy$C_{1-6}$alkyl, particularly carboxymethyl or carboxyethyl; $C_{1-6}$alkylcarbonyl, particularly acetyl; $C_{1-6}$alkyloxycarbonyl$C_{1-6}$alkyl or carboxy-$C_{1-6}$alkyloxy$C_{1-6}$alkyl, particularly carboxymethoxypropyl or carboxyethoxypropyl; $C_{1-6}$alkylcarbonyloxy$C_{1-6}$alkyl, particularly 2-acetyloxypropyl. Especially noteworthy as complexants and/or solubilizers are β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD).

The most preferred cyclodextrin derivative for use in the compositions of the present invention is 2-hydroxypropyl-β-cyclodextrin having an average molar substitution (M.S.) in the range of from 0.35 to 0.50 (determined by mass spectrometry) and containing less than 1.5% unsubstituted β-cyclodextrin. M.S. values determined by NMR or IR preferably range from 0.55 to 0.75.

The pharmaceutical compositions may consist of only the compound of formula (I) and the cyclodextrin or cyclodextrin derivative. This solid form can conveniently be prepared by lyophilization of an aqueous solution, or alternatively, by co-precipitation. This formula is particularly useful for reconstitution with water, saline or an aqueous solution of the cyclodextrin, or for compounding with non-pharmaceutical liquids such as fruit juice, or even solids such as food.

Preferably, the pharmaceutical compositions according to the invention are suitable for oral administration.

The compositions may advantageously be presented in discrete dose units, especially in unit dosage forms. A convenient unit dose formulation contains the active ingredient in an amount of from 0.1 to 100 mg. The amount of a compound of formula (I) required as daily dose in treatment will vary not only with the particular compound selected, but also with the route of administration, the nature of the condition being treated and the age, weight and condition of the patient and will ultimately be at the discretion of the attendant physician. In general, however, a suitable dose will be in the range of from about 0.5 to about 20 mg per day. A suitable daily dose for use in prophylaxis will generally be in the same range.

The desired dose may conveniently be presented in a single dose or as divided doses administered at appropriate intervals, for example as two, three, four or more sub-doses per day. The daily dose of N-cycloheptyl-2,3-dihydroimidazo[2,1-b]benzothiazol-7-amine can be administered in single dose (o.d.), but is preferably administered in two doses (b.i.d.), because such a regimen yields effective plasma levels over a period of 24 hours. Upon reiterated or chronic administration, plasma levels will progressively increase until a steady state is reached.

The compounds of formula (I) may also be used in combination with other agents used in the treatment or palliation of neurodegenerative disorders, for example, agents that substitute for the loss of neurotransmitters, such as dopaminergic loss, e.g. levodopa; but in particular the cholinergic loss, e.g. galanthamine, E 2020, physostygmine or tacrine; memory-enhancing drugs, e.g. sabeluzole; agents used in combatting AIDS such as nucleoside reverse transcriptase inhibitors, e.g. zidovudine (AZT), didanosine (ddI), zalcitabine (ddC), lamivudine (3TC), stavudine (24T); non-nucleoside reverse transcriptase inhibitors, e.g. loviride, nevirapine (pyridinone), 8-chloroTIBO or tivirapine ((−)-(S)-8-chloro-4,5,6,7-tetrahydro-5-methyl-6-(3-methyl-2-butenyl)imidazo[4,5,1-jk][1,4]benzodiazepine-2(1H)-thione monohydrochloride), HIV-protease inhibitors, e.g. saquinavir, indinavir, nelfinavir, ritonavir, and the like antiretroviral compounds; anti-oxidants such as Vitamin C, Vitamin E, probucol and the like agents.

The invention thus provides in a further aspect a combination comprising a composition comprising a pharmaceutically acceptable carrier and as active ingredient: (a) an effective amount of a compound of formula (I) as defined herein, together with: (b) an effective amount of another therapeutically active agent as defined in the preceding paragraph. The combination may be administered separately, i.e. simultaneously, concurrently or consecutively by any of the routes described above, or the combination may also be presented in the form of one pharmaceutical formulation. Thus, a pharmaceutical product comprising (a) a compound of formula (I) and (b) another therapeutic agent as defined hereinbefore, as a combined preparation for simultaneous, separate or sequential use in the therapeutic or prophylactic treatment of humans suffering from ageing of, or degenerative diseases of the nervous or vascular system which are associated with oxidative stress, comprises a further aspect of the invention. Such a product may comprise a kit comprising a container containing a pharmaceutical composition of a compound of formula (I), and another container comprising a pharmaceutical composition of the second therapeutic agent. The product with separate compositions of the two active ingredients has the advantage that appropriate amounts of each component, and timing and sequence of administration can be selected in function of the patient.

When compounds of formula (I) are used in combination with a second therapeutic agent, the dose of each compound may vary from that when the compound is used alone. Thus when compounds of formula (I) are used together with a second therapeutic agent the dose of each compound may be the same or more commonly, lower, than that employed when the compound is used alone. Appropriate doses will be readily appreciated by those skilled in the art.

EXAMPLE 1
In Vitro Protection Against Glutathione Depletion

Human fibroblasts [strain NS] were cultured in cystine/methionine deficient EMEM for 48 hr. In control cultures not receiving any treatment, all cells became necrotic. Cell death was scored by phase contrast microscopy. Table 1 summarizes the $EC_{90}$ values observed with the compounds of formula (I), i.e. the concentration at which more than 90% of the fibroblasts survive 48 hours after treatment with a compound of formula (I).

TABLE 1

| Co. No. | $R^1$ | $R^2$ | $EC_{90}$ [M] |
|---|---|---|---|
| 1 | 1-propyl | H | $4 \cdot 10^{-5}$ |
| 2 | methyl | H | $2 \cdot 10^{-4}$ |
| 3 | cyclohexyl | H | $4 \cdot 10^{-5}$ |
| 4 | cyclopentyl | H | $4 \cdot 10^{-5}$ |
| 5 | 2-propyl | H | $4 \cdot 10^{-5}$ |
| 6 | methyl | methyl | $4 \cdot 10^{-5}$ |
| 7 | cycloheptyl | H | $3.2 \cdot 10^{-7}$ |
| 8 | ethyl | H | $2 \cdot 10^{-4}$ |
| 9 | 3-pentyl | H | $4 \cdot 10^{-5}$ |
| 10 | 1-butyl | H | $2 \cdot 10^{-4}$ |
| 11 | 2-butyl | H | $4 \cdot 10^{-5}$ |
| 12 | 2-pentyl | H | $4 \cdot 10^{-5}$ |
| 13 | 2-hexyl | H | $8 \cdot 10^{-6}$ |
| 14 | 2,2-dimethylpropyl | H | $8 \cdot 10^{-6}$ |
| 15 | 1-propyl | 1-propyl | $4 \cdot 10^{-5}$ |
| 16 | 1-hexyl | H | $1.6 \cdot 10^{-6}$ |

EXAMPLE 2

Primary embryonic hippocampal cultures were prepared essentially as described previously (Pauwels, P, Van Aschouw, H. P., Peeters, L., Moeremans, M., Leysen, J. E. 1992. Chronic treatment with sabeluzole protects cultured rat brain neurons from the neurotoxic effects of excitatory amino acids. Synapse, 12:271–280). Hippocampal formations of rats at embryonic day 17 were dissected and dissociated in 0.05% trypsin, 0.1 mg/ml DNase I in DMEM (Dulbecco Modified Eagle Medium). Heat-inactivated horse serum (HS) was added to a concentration of 4%, and the cells were centrifuged, washed with DMEM, and resuspended in DMEM/Ham's F12 (3:1) containing 10% HS. The cells were plated at a density of $4 \times 10^5$ cells/cm² in poly L-lysine (0.001%) pre-coated multiwell-24 plates. On day 1 in culture, the medium was changed to chemically defined CDM-R12 medium (DMEM-HEPES/Ham's F12 (3:1) containing 0.26% bovine serum albumin, 30 nM sodium selenite, 3 nM 3,3',5 triiodo-L-thyronine, 0.35 $\mu$M retinol, 0.3 $\mu$M retinol acetate, 2.3 $\mu$M DL-a-tocopherol, 2.1 $\mu$M DL-α-tocopherol acetate, 3.6 4 $\mu$M linolenic acid, 3.6 $\mu$M linoleic acid, 0.125% human transferrin, 20 nM progesterone, 57.7 nM corticosterone, 49 U/l insulin, 0.4 $\mu$M biotin, 10 $\mu$M L-carnitine, 83 $\mu$M D(+)-galactose, 3.3 $\mu$M glutathione, 10 $\mu$M ethanolamine, 0.1 mM putrescine; Romijn, H. J., van Huizen, F., Wolters, P. S. 1984. Towards an improved serum-free, chemically defined medium for long-term culturing of cerebral cortex tissue. Neurosci. Behav. Rev., 8:301–334), either with (control) or without DL-α-tocopherol (VitE) and DL-α-tocopherol acetate, in the presence or absence of test compound. When vitE was omitted from the culture medium, severe cell death was observed at 4 days in vitro. Addition of compounds could rescue the cultures. Culture survival was measured by means of cytoplasmic LDH activity. The $EC_{50}$ for survival-rescue in vitE depleted cultures refers to the concentration of the compound required to restore culture survival to 50% of the survival seen for the culture grown in vitE supplemented medium. Seven concentrations of each compound were tested in triplicate, the number of independent experiments is indicated in the table, and the mean $EC_{50}$-value $\pm$ SD was calculated (Table 2).

Primary neuronal cultures depend on the presence of the antioxidant vitE in the culture medium for survival in vitro. When vitE depleted medium is used to grow the cultures, survival drops to $\pm 20\%$ of control. Compounds with antioxidative properties are able to complement the lack of vitE, and as such can when added to the culture medium, rescue vitE devoid cultures. Several derivatives of formula (I) were tested at $10^{-7}$ M and $10^{-6}$ M in the vitE depletion test on primary neuronal cultures, and were all able to rescue survival of vitE depleted cultures to a certain extent (Table 2).

Compound 7 was the most potent compound: complete rescue of primary neuronal cultures grown in VitE depleted medium was seen at $10^{-7}$ M. The concentration of Compound 7 at which the culture was rescued to 50% of control (control is a culture grown in medium containing 4.4 $\mu$M vitE) was $25 \pm 12$ nM (Table 2). Based on these data, the antioxidative activity of Compound 7 in the above test is estimated to be about 100 times more potent than that of vitE.

TABLE 2

$EC_{50}$ values in nM for survival-rescue in vitE depleted cultures.

| Co. No. | $R^1$ | $EC_{50}$ in nM, mean $\pm$ SD (number of dose responses) |
|---|---|---|
| 3 | c-hexyl | 120 $\pm$ 71 (4) |
| 4 | c-pentyl | 177 $\pm$ 59 (3) |
| 7 | c-heptyl | 25 $\pm$ 12(5) |
| 11 | 2-butyl | 224 (1) |
| 12 | 2-pentyl | 370 $\pm$ 169 (2) |
| 13 | 2-hexyl | 45 (1) |
| 16 | 1-hexyl | 41 $\pm$ 18 (4) |
| 17 | 2-adamantyl | 47 $\pm$ 19 (4) |

| Co. No | $R^1$ | $R^3$ | $R^5$ | $EC_{50}$ in nM, mean $\pm$ SD (number of dose responses) |
|---|---|---|---|---|
| 18 | c-pentyl | methyl | 2-propyl | 126 (1) |

EXAMPLE 3

Competitive inhibition by glutamate of cystine uptake in certain cells leads to glutathione (GSH) depletion and oxidative stress. This oxidative stress model has been described for glial C6 glioma cells (Kato et al., 1992. A mechanism for glutamate toxicity in the C6 glioma cells involving inhibition of cystine uptake leading to glutathion depletion. Neurosci. 48:903–914) and for the neuronal cell line N18RE105 (Murphy et al., 1989. Glutamate toxicity in a neuronal cell line involves inhibition of cystine transport leading to oxidative stress. Neuron 2:1547–1558).

Cell culture: C6 glioma cells (American Type Culture Collection, CCL 107) were cultivated in DMEM supplemented with 2~4 mM glutamine, 1 mM pyruvate and 5~10% heat-inactivated foetal calf serum. Cultures were maintained at 37° C. in an air/5~10% $CO_2$, water saturated atmosphere.

Glutathione depletion and evaluation of drugs as antioxidants: Experiments were carried out with cultures plated at 30,000~50,000 cells/cm² in 24-well culture plates (for toxicity and peroxide measurements) or at 136,000 cells/cm² in 96well culture plates (for GSH determination). After 8–24 hr, the cultures were switched to culture medium in the absence or presence of the GSH depleting compound glutamate (10 mM). In order to test drugs for inhibition of oxidative stress, the drug was added together with glutamate (final concentration of solvent was 0.01% hydroxypropyl-β-cyclodextrin, 0.1% DMSO). Intracellular GSH levels were measured after 6~8 hr, intracellular peroxides were measured after 14~20 hr, and toxicity and protection were analysed after 48 hr using the lactate dehydrogenase (LDH) assay according to the method of Bergmeyer and Bernt (UV-assay with pyruvate and NADH. In: Methods of Enzymatic Analysis. 1974. H. U. Bergmeyer, ed. Acad. Press, New York, 2nd Ed., pp 574–579).

Determination of GSH content in C6 glioma cell culture: GSH levels were analysed by a micro method, essentially as described by Vandeputte et al. (1994), with a modification in the washing and homogenisation procedure. Cells (in 96-well plates) were washed with PBS, were homogenised in 50 μl 10 mM HCl containing 1.3% 5-sulfosalicylic acid, and the homogenate was centrifuged at 1200×g for 10 min at 4° C. Forty μl of the supernatant was transferred to a well of a 96well plate and 200 μl reagent (1 mM DTNB [5,5'-dithiobis-(2-nitrobenzoic acid)] and 0.34 mM NADPH and 6.3 mM EDTA in 143 mM phosphate buffer pH 7.4) was added. After 5 min equilibration to room temperature the reaction was started by adding 40 μl GSH reductase (8.5 IU/ml 143 mM phosphate buffer, 6.3 mM EDTA pH 7.4). NADPH oxidation was followed at 414 nm for 5 minutes with a Multiskan MCC/340 (Labsystems), and the change in absorbency (ΔA) per min was calculated. The GSH content was deduced from a standard curve ranging from 0.2 to 2 nmol commercial GSH per test (ΔA/min plotted versus concentration).

Fluorescence measurement of intracellular peroxides: Formation of intracellular peroxides was detected using 6-carboxy-2',7'-dichlorodihydrofluorescin diacetate, di(acetoxymethyl ester) (C-DCDHF, Molecular Probes). C-DCDHF was dissolved in DMSO at a concentration of 10 mM and stored at −70° C. under nitrogen. After exposure of the culture to 10 mM glutamate for 14~20 hr, the cells were loaded with 100 μM fluorophore for one hour at 37° C. Medium was aspirated off, PBS was added to the cells, and plates were read in a Cytofluor II micro plate fluorescence reader (PerSeptive Biosystems). Excitation and emission wavelength were selected with a 485/530 nm filter pair. Fluorescence intensity, expressed in relative fluorescence units (rfu)/μg cellular protein was used as index of intracellular peroxides.

Results: Treatment of C6 glioma cell cultures with 10 mM glutamate for 6~7 hr led to a reduction in intracellular GSH levels (Table 3), to about a 3-fold lower level than the level in control wells (277 pmol GSH/well versus 919 pmol GSH/well). The reduction in GSH resulted in oxidative stress, as indicated by a ±3-fold increase in toxic intracellular peroxides (increase from 69 rfu/μg protein to 205 rfu/μg protein). Ultimately ±78% cell death occurred after 16 to 48 hr. Excitotoxicity was not involved in this toxicity, as LDH release (an index of cellular toxicity) was not prevented by the NMDA antagonist MK801 (data not shown). Under our culture conditions (Table A) basal LDH release in C6 glioma cultures was 11±3% of total LDH (mean ± SEM, n=7), and LDH release after 48 hr treatment with 10 mM glutamate was 78±7% of total LDH. Compound 7 fully protected these cultures from cell death at 1 μM (Table 3). This protection was not due to restoration of GSH levels, which remained about one third of the solvent control level. Protection paralleled the inhibition of glutamate-induced intracellular peroxidation, indicating that protection by Compound 7 was the result of an interference with GSH-depletion-induced oxidative stress. Dose response analysis (Table 4) revealed a high potency of Compound 7 for protection against oxidative stress-induced cell toxicity ($IC_{50}$ 9 nM) and a high potency for inhibition of oxidative stress-induced intracellular peroxidation. Evaluation of structurally related compounds (Table 5), indicated that they showed similar activities.

Conclusion: This is clear in vitro evidence that Compound 7 as well as some closely related compounds act in cell culture as potent antioxidants; they protect cells from oxidative stress-induced cell death, as they inhibit the oxidative stress-induced increase in toxic intracellular peroxides.

TABLE 3

Inhibition of glutathione depletion-induced intracellular peroxidation and cell toxicity in C6 glioma cells

| Treatment | LDH release, % of total (mean ± SEM, n = 7) | GSH level, pmol/well (mean ± SEM, n = 3) | Intracellular peroxides, rfu/μg protein* (mean ± SEM, n = 5) |
|---|---|---|---|
| Solvent | 11 ± 3 | 919 ± 166 | 69 ± 14 |
| Glutamate, 10 mM | 78 ± 7 | 277 ± 24 | 205 ± 35 |
| +Compound 7, 1 μM | 15 ± 4 | 242 ± 54 | 67 ± 16 |

TABLE 4

Inhibition of glutathione depletion-induced oxidative stress in C6 glioma cells

| Compound | Protection $IC_{50}$, nM (mean ± SEM, n = 3) | Inhibition of intracellular peroxides $IC_{50}$, nM (individual values of 2 experiments) |
|---|---|---|
| 7 | 9 ± 1 | 28 and 71 |

TABLE 5

Inhibition of glutathione depletion-induced oxidative stress in C6 glioma cells

| Compound | Protection IC$_{50}$, nM, (mean ± SEM, n = 3) | Level of intracellular peroxides rfu/µg protein (mean ± SEM, n ≥ 3, 1 µM compound) |
|---|---|---|
| Solvent control | — | 21 ± 1 |
| Glutamate, 10 mM | — | 86 ± 4 |
| +3  | 18 ± 3  | 22 ± 2 |
| +4  | 29 ± 7  | 18 ± 2 |
| +17 | 12 ± 2  | 19 ± 1 |
| +12 | 29 ± 14 | 24 ± 1 |
| +13 | 10 ± 5  | 19 ± 1 |
| +16 | 5 ± 1   | 21 ± 1 |
| +18 | 25 ± 14 | 19 ± 1 |

We claim:

1. A method for the therapeutic or prophylactic treatment of diseases and conditions associated with oxidative damage or injury selected from the group consisting of thromboembolic stroke, cerebral stroke, haemorrhagic stroke, cerebral ischaemia, cerebral vasospasm, cerebral ageing, cerebral or spinal trauma, cardiac arrest, arterial hypotension, cardiac or pulmonary surgery, severe hypoglycemia, anoxia, hypoxia, and perinatal asphyxia, comprising administering to a host in need thereof an effective amount of a compound of the formula

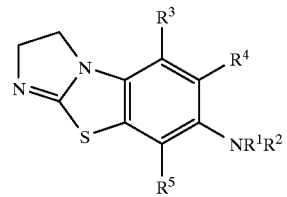

wherein $R^1$ represents $C_{1-10}$ alkyl or $C_{5-12}$ cycloalkyl,
$R^2$ represents hydrogen or $C_{1-10}$ alkyl; and
$R^3$, $R^4$ and $R^5$ each independently represent hydrogen or $C_{1-4}$ alkyl.

2. The method of claim 1 wherein $R^1$ represents $C_{4-10}$alkyl or $C_{7-12}$cycloalkyl; and $R^2$ represents hydrogen.

3. The method of claim 1, wherein $R^3$, $R^4$ and $R^5$ represent hydrogen and $R^3$ and $R^5$ also may represent methyl, ethyl, 2-propyl and 2-methyl-2-propyl.

4. The method of claim 1 wherein $R^1$ represents a straight $C_{6-10}$alkyl group, a $C_{4-10}$alkyl group branched in α- or β-position or a monocyclic $C_{7-10}$cycloalkyl group.

5. The method of claim 1 wherein the compound of formula (I) is N-cycloheptyl-2,3-dihydro-imidazo[2,1-b]benzothiazol-7-amine dihydrochloride.

6. The method of claim 4 wherein the compound of formula (I) is used for the manufacture of a pharmaceutical composition adapted for oral administration.

7. The method of claim 5 wherein the N-cycloheptyl-2,3-dihydro-imidazo[2,1-b]benzothiazol-7-amine dihydrochloride is administered in a daily dosage range of from 0.1 to 20 mg.

8. The method of claim 6, wherein the compound of formula (I) is given as a daily dosage in a single administration.

9. The method of claim 8, wherein the condition is cerebral stroke.

* * * * *